US008906079B2

United States Patent
López D'Ambola et al.

(10) Patent No.: US 8,906,079 B2
(45) Date of Patent: Dec. 9, 2014

(54) METHOD/DEVICE FOR TRANSDERMAL VASCULAR TREATMENT

(75) Inventors: Jorge O. López D'Ambola, Mendoza (AR); Jorge E. Soracco, Capital Federal (AR); Wolfgang Neuberger, Dubai (AE)

(73) Assignee: Biolitec Pharma Marketing Ltd, F.T. Lebuan (MY)

( * ) Notice: Subject to any disclaimer, the term of this patent is extended or adjusted under 35 U.S.C. 154(b) by 449 days.

(21) Appl. No.: 12/992,533

(22) PCT Filed: May 15, 2009

(86) PCT No.: PCT/US2009/003029
§ 371 (c)(1),
(2), (4) Date: Dec. 8, 2010

(87) PCT Pub. No.: WO2009/139900
PCT Pub. Date: Nov. 19, 2009

(65) Prior Publication Data
US 2011/0275979 A1    Nov. 10, 2011

Related U.S. Application Data

(60) Provisional application No. 61/127,918, filed on May 15, 2008.

(51) Int. Cl.
*A61N 5/06* (2006.01)
*A61B 18/20* (2006.01)
*A61B 18/22* (2006.01)
*A61B 18/00* (2006.01)
*A61N 5/00* (2006.01)
*A61B 17/00* (2006.01)

(52) U.S. Cl.
CPC ............... *A61B 18/203* (2013.01); *A61B 18/20* (2013.01); *A61B 18/22* (2013.01); *A61B 2018/00452* (2013.01); *A61B 2018/00458* (2013.01); *A61B 2018/202* (2013.01); *A61N 2005/007* (2013.01); *A61N 2005/0651* (2013.01); *A61N 2005/0659* (2013.01); *A61N 5/062* (2013.01); *A61B 2017/00765* (2013.01); *A61B 2018/2065* (2013.01)
USPC ............................................. 607/88

(58) Field of Classification Search
USPC ................... 128/898; 606/2–19; 607/88–94
See application file for complete search history.

(56) References Cited

U.S. PATENT DOCUMENTS

| 7,160,289 B2* | 1/2007 | Cohen ............................. 606/9 |
| 2005/0010198 A1* | 1/2005 | Marchitto et al. ............... 606/9 |

(Continued)

*Primary Examiner* — Aaron Roane
(74) *Attorney, Agent, or Firm* — Bolesh J. Skutnik; BJ Associates (57) ABSTRACT

Devices and transdermal methods are provided for safe and effective therapeutic treatment of the venous system, such as varicose veins. Present invention provides non-invasive and minimally invasive transdermal methods for treating varicose and spider veins, comprising the use of a radiation source in combination with a chemical fluid/composition to safely and more effectively close or shrink vein walls, providing a transdermal therapeutic method for varicose veins until now only treated with surgery or endovascular laser treatments. In a preferred embodiment a device comprises a radiation source, preferably of wavelength between about 980 and 1940 nm, being effective in causing shrinkage of the vein treated. In other preferred embodiments methods comprise the transdermal delivery of a chemical composition through a patch or gel or the injection of a chemical fluid, preferably a hypertonic solution, to the vein under treatment; and simultaneously or after a dwell time, irradiating with a radiation source transdermally. The treatment performed with the present invention results in blood vessel wall damaged, eventually closing the vein, in lesser time with practically no pain or discomfort to the patient during and after the therapy.

10 Claims, 5 Drawing Sheets

(56) References Cited

U.S. PATENT DOCUMENTS

| | | | |
|---|---|---|---|
| 2005/0215988 A1* | 9/2005 | Altshuler et al. | 606/9 |
| 2006/0259102 A1* | 11/2006 | Slatkine | 607/88 |
| 2007/0100329 A1* | 5/2007 | Maglione et al. | 606/15 |
| 2007/0282248 A1* | 12/2007 | Navarro et al. | 604/21 |

* cited by examiner

METHOD/DEVICE FOR TRANSDERMAL VASCULAR TREATMENT

NATIONAL FILING UNDER 35 USC 371

This application is being filed as a US National stage under 35 USC 371 of PCT Application No. PCT/US09/03029, which was filed May 15, 2009 and also claims the benefit of U.S. Provisional Application Ser. No. 61/127,918 filed May 15, 2008, both of which are incorporated by reference herein.

BACKGROUND OF THE INVENTION

1. Field of the Invention

The invention is related to the field of phlebology, mainly involved in therapeutic treatments of the venous system. More particularly, the invention is related to a non-invasive method including the use of a light source in combination with chemical therapy for treatment of venous disorders, such as varicose veins and telangiectasias.

2. Information Disclosure Statement

Frequently, a considerable number of men and women suffer from venous system pathologies, including varicose and spider veins. Varicose veins alone affect up to 60 percent of older people.

Varicose veins refer to blood vessels that have become enlarged and twisted and have progressively lost their wall elasticity. Owing to the widening of the blood vessels, vein valves cannot be completely closed and veins lose their ability to carry blood back to the heart. This leads to an accumulation of blood inside the vessels, enlarging and twisting the veins even more. Furthermore, varicose veins usually have a blue or purple color and may protrude above the surface of the skin, being responsible for their characteristically unattractive appearance. They are commonly formed in the superficial veins of the legs, which are subject to high pressure when standing. Other types of varicose veins include reticular veins, phlebectasias and telangiectasias These vein disorders generally consists of thin, dark-colored, small dilated blood vessels that lie close to the surface of the skin. The dilated small veins often have a web or sunburst pattern, but may also appear as random line segments. They can develop anywhere on the body but most commonly on the lower limbs, typically on the upper thigh, below the knee joint, and around the ankles, and also on the face around the nose, cheeks, and chin and on the back of the hands.

There are a number of symptoms associated with varicose and spider veins, such as aching, itching, burning, swelling, feeling of heaviness in the legs, throbbing and muscle cramping. Even though some patients are asymptomatic they treat varicose or spider veins for cosmetic reasons. Nevertheless, in some cases varicose veins have more serious complications including thrombophlebitis, dermatitis, hemorrhage, inflammation and ulcers. Usually, with varicose veins, phlebitis may occur spontaneously or as a result of an injury. Moreover, scratching when it itches may cause bleeding or development of a painful ulcer that does not heal.

There are a number of treatments available intended to eradicate these kinds of vascular pathologies. Some of the treatments relieve the symptoms but do not prevent new varicose veins from forming. Such treatments may include elevating the legs by lying down or using a footstool when sitting, use of elastic stockings and exercise.

Surgical treatments are an alternative available treatment. Some surgical therapies consist of the removal of the vein by: 1) stab avulsion phlebectomy, where the vein is removed by making a series of incisions, inserting a hook, gripping and pulling out the affected vein; 2) vein stripping, a procedure that involves making two incisions and tearing out the vein axis using a wire; 3) catheter-assisted procedures, where a catheter is inserted into the vein to be treated. Its tip is heated, and then, as the catheter is pulled out, the heat causes vein ablation.

Use of surgical therapies has several disadvantages compared to other approaches. One of them is the need for general, local or peridural anesthesia. Furthermore, these procedures may damage collateral branches of the vein which may consequently bleed, giving rise to hematomas, or may lead to other complications such as blood loss, pain, infection, nerve injury or swelling. Moreover, because of the damage done to the treated area, patients may suffer pain and discomfort during hours or days after surgery. Fortunately, there is another surgical option for the treatment of blood vessels namely, laser surgery, which has been improved due to new diode laser equipments. Endovascular laser surgery consists of applying laser radiation and providing thermal (or photothermal) energy to the vein wall with the aid of an optical fiber. While the optical fiber is withdrawn the vein closes and the blood vessel irreversible evolves into fibrotic tissue.

However, surgery is not the only option. There are some non-surgical treatments like sclerotherapy, that have been used for treating varicose veins for almost 150 years. In US Patent Application US 2006/0106350A1 by Spitz titled "Apparatus and Methods for Treating Undesired Veins", methods and apparatus for treating undesired veins are disclosed. A typical treatment session consists of introducing the sclerosing agent inside the vein to be treated. Once the sclerosing agent is inside the vein, it begins to irritate the internal lining of the blood vessel, causing inflammation and, eventually clotting and scaring. Depending on the concentration and strength of the sclerosing solution, between 30 to 40 syringes may be needed. One of the main disadvantages of sclerotherapy treatments is the pain associated with the use of syringes and the resulting discomfort of patients.

Nowadays, there are some treatments that include both sclerotherapy and laser treatments in order to improve therapies available for treating vascular pathologies. In an attempt to improve the combination of sclerotherapy and laser light in the treatment of superficial venous pathologies Navarro et al. disclosed a treatment for spider veins in US Patent Application US 2007/0282248A1 and International Patent Application WO 2007/131199A2 titled "Cosmetic Method and Kit for Treatment of Spider Veins and Other Superficial Venous Pathology"; and varicose veins in US Patent Application US 2007/0260229A1 titled "Method and Kit for Treatment of Varicose Veins and Other Superficial Venous Pathology". The procedure consists of piercing the vein to be treated percutaneously, and then, following the sclerotherapy treatment or after a dwell time, laser light is directed to the area of the patient's skin affected by the piercing step. Multiple non-hypertonic sclerosing agents and/or chromophores injections may be used. Despite the combination of treatments one of its main disadvantages is that the sclerosing agents used in this invention may cause an allergic reaction, thus limiting their use. Moreover, to obtain an efficient therapy the treatment area needs to exhibit ecchymosis. This leads to unpleasant patient discomfort due to swelling and pain associated with bruises in general. Moreover, after directing light, not only the target vein is degraded but also the whole area with extravasated blood, requiring wound dressings to treat the area after the procedure is completed.

Instead of using a sclerosing agent, a device for removing visible veins on the leg with indocyanine green as a chromophore is disclosed by Abels et al. in U.S. Pat. No. 6,491, 715 titled "Device for Treating Growing, Dilated or Malformed Blood Vessels and Method for Treating Biological Material". The device has a control unit which controls the power of the laser depending on the concentration of chromophore in the patient. One of the main disadvantages of this treatment is that the chromophore needs to be uniformly distributed in the whole vascular system prior to laser treatment, not just in the area that needs to be treated. Moreover, commercial indocyanine green may cause an allergic reaction, thus limiting its extensive use. In addition, the treatment requires the delivery of laser radiation pulses of powers as high as 100 to 800 Watts; thus not only malformed vessels are heated but also the tissue surrounding the treated vessel may be damaged. Furthermore the device needs two lasers, one for therapy and the other one for determining chromophore concentration, becoming an expensive and voluminous device not always easy to place in an operating theatre.

Another attempt to eliminate varicose veins using laser radiation and a photodynamic sclerosis composition is disclosed in International Patent Application WO 2007/133525 A2 by Castro et al., having the same assignee as the present invention, titled "Photodynamic Foam Composition and Sclerosis Treatment". The photodynamic sclerosis composition is a foam that comprises a photosensitizer, a detergent and a glucose solution. The method consists of introducing the photodynamic sclerosis composition into the vein to be treated and after a sufficient time, applying radiation of appropriate wavelength absorbed by the composition, to activate the photosensitizer. According to the patent, the invention allows for full control of the drug concentration inside the vein, improved time of contact between the sclerosing agent and the endothelium, increased intimate destruction and quicker transformation of the varicose veins into a fibrotic cord and its posterior elimination, by phagocytosis. Nevertheless, for an effective treatment the photodynamic sclerosis composition comprises a detergent solution known as polydodecanol, a sclerosing agent, which may often induce dark cutaneous pigmentations, more frequently for small vessels, such as telangiectasia.

Therefore there is a need for an effective treatment capable of overcoming the main disadvantages of other therapies currently available for treating venous pathologies, such as varicose and spider veins. Moreover, there is a need for an ambulatory painless treatment, able to provide fast recovery and improved therapeutic results, without generating serious potential side effects, not causing allergic reactions and with no anesthesia requirements. The present invention addresses this need.

OBJECTIVES AND BRIEF SUMMARY OF THE INVENTION

In the broadest sense, it is the aim of this invention to provide devices and non-invasive and minimally invasive methods for treatment of the venous system, such as varicose and spider veins.

It is another objective of the present invention to provide devices and methods for therapeutic transdermal treatment of the venous system.

It is yet another objective to offer transdermal methods comprising the use of a light source and a chemical fluid/composition for treatment of the venous system, such as varicose veins.

It is still another objective to provide a chemical composition to be delivered transdermally before electromagnetic radiation is directed to the vein.

It is a further objective to provide a chemical fluid to be delivered during electromagnetic irradiation, occurring while the chemical fluid is injected into the vein to be treated.

A still further objective is to offer a chemical fluid/composition that may damage and/or irritate the vein wall or endothelium such as a chromophore that absorbs the electromagnetic radiation delivered, a hypertonic solution and/or a combination of both.

It is still another objective to provide a device for transdermal treatment where the electromagnetic radiation source is preferably a laser, preferentially a diode laser, where radiation wavelengths delivered by the equipment are effectively absorbed by the chemical fluid/composition used in the present invention.

Briefly stated the present invention provides devices and transdermal methods for safe and effective therapeutic treatment of the venous system, such as varicose veins. Present invention provides non-invasive and minimally invasive transdermal methods for treating varicose and spider veins, comprising the use of a radiation source in combination with a chemical fluid/composition to safely and more effectively close or shrink vein walls, providing a transdermal therapeutic method for varicose veins until now only treated with surgery or endovascular laser treatments. In a preferred embodiment a device comprises a radiation source, preferably of wavelength between about 980 and 1940 nm, being effective in causing shrinkage of the vein treated. In other preferred embodiments, methods comprise transdermal delivery of a chemical composition through a patch or gel or the injection of a chemical fluid, preferably a hypertonic solution, to the vein under treatment; and simultaneously or after a preselected dwell time, irradiating with a radiation source transdermally. The treatment performed with the present invention results in blood vessel wall damage, eventually closing the vein, in lesser time with practically no pain or discomfort to the patient during and after the therapy.

The above and other objects, features and advantages of the present invention will become apparent from the following description read in conjunction with the accompanying drawings, (in which like reference numbers in different drawings designate the same elements.)

DETAILED DESCRIPTION OF PREFERRED EMBODIMENTS

The present invention comprises devices and methods for treating varicose veins transdermally combined with a suitable chemical fluid/composition, resulting in partially shrinking or completely closing varicose veins. With this invention, the varicose blood vessel wall is damaged, reducing its diameter and in a few sessions, it changes into fibrotic tissue, thus closing the vein. Eventually the fibrotic tissue is absorbed by the body. Moreover, the present invention gives an ambulatory transdermal treatment for treating varicose veins superior than prior art techniques, as it reduces discomfort to the patient and offers less time consuming procedures. Moreover, it provides an efficient transdermal method that allows the treatment of varicose and spider veins with a diameter that until now could be only treated with surgery or endovascular laser treatments.

In a preferred embodiment, a device for transdermal treatments comprises a radiation source, preferably a radiation source of wavelength about 980 and 1940 nm. This range is preferred because within these wavelengths radiation energy has moderate absorption in both water and tissue melanin and provides adequate tissue penetration with sufficient energy to heat water inside vessels and denature proteins, such as collagen, in the target vein walls. Additionally, water absorption inside target vessels can be enhanced by the chemical fluid/composition delivered prior to irradiation of the target vein. Furthermore, due to the low absorption of radiation energy by melanin between 980 and 1940 nm, there is no ecchymosis, hematomas nor hyper-pigmentation of the skin while and after performing a transdermal treatment of varicose veins and telangiectasias. Radiation source includes coherent and incoherent radiation sources such as laser radiation sources, light emitting diode sources, lamp radiation source (incandescent, xenon arc and metal halide lamps) and/or other radiation sources from the environment, whose output is or can be regulated within the selected spectral window.

Figure 1:
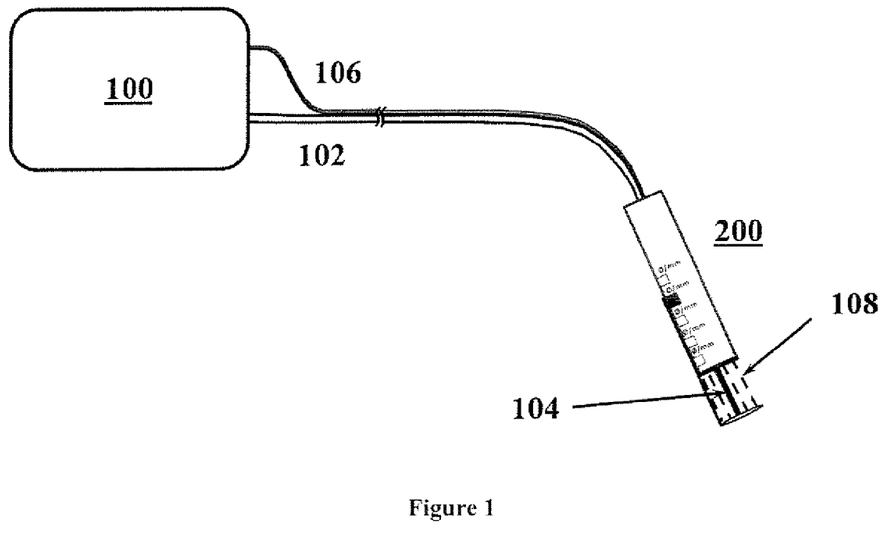
FIG. 1 depicts an embodiment of a device for transdermal treatment of varicose veins.
Figure 2A:
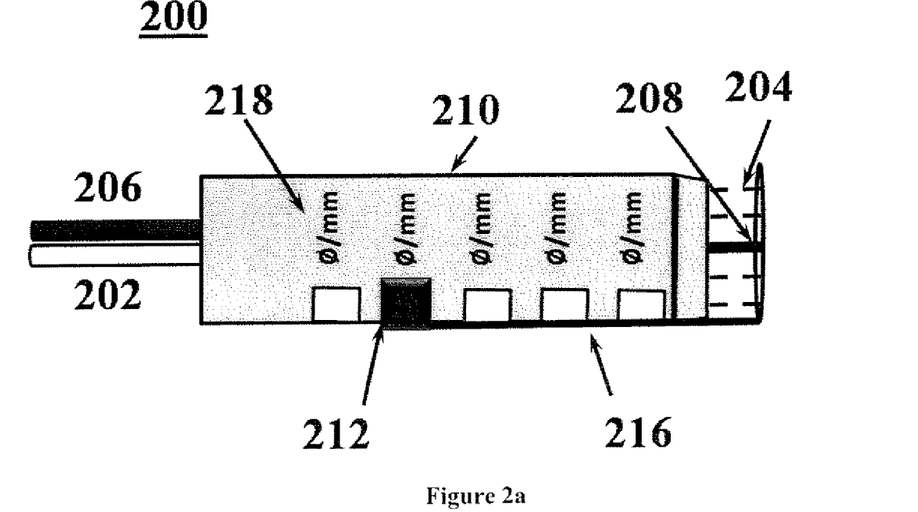
FIG. 2a represents an embodiment of a handpiece for delivering laser radiation to the treated area.
Figure 2B:
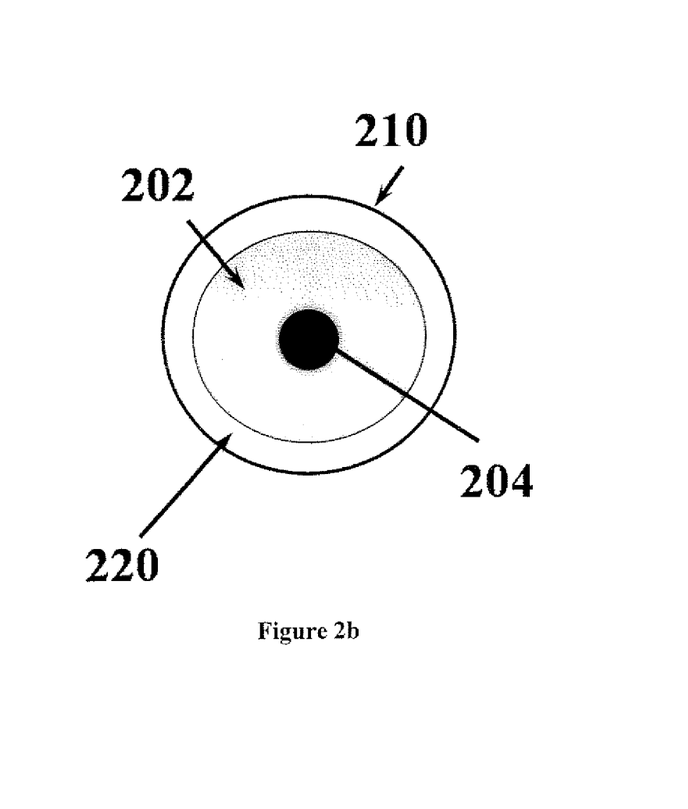
FIG. 2b shows a frontal view of the embodiment from FIG. 2a of the distal end of a handpiece for delivering laser radiation to the treated area.

In another embodiment, see FIGS. 1 and 2, a device for transdermal treatments comprises a radiation source 100, preferably a laser radiation source of wavelength between about 980 and 1940 nm and handpiece for transdermal laser energy delivery. Laser radiation is transmitted from the laser source to the handpiece with the aid of waveguide 102, such as a laser optical fiber. Simultaneously or after a dwelling time, laser radiation 104 is delivered to the treated zone with the aid of handpiece 200. Preferably, handpiece 200 has cooling system 106 associated that allows for cooling the skin while lasing. Preferably, cooling system 106 delivers cooling fluid 108 through handpiece 200, concentrically to laser radiation 104. FIG. 2a shows a preferred embodiment of handpiece 200 used to deliver laser radiation 204 and cooling fluid 208 onto the skin, where a preferable fluid is air. Handpiece 200 is connected to waveguide 202, preferably an optical fiber, and cooling system 206. Handpiece 200 includes space limiting accessory 216 which can be regulated in distance relative to the skin, to determine a desired laser spot. This can be done by locking the proximal end of space limiting accessory 216 to any of slots 212 located on handpiece outer case 210. Preferably, scale 218 on handpiece 200 is used to show the distance from the emitting end of handpiece 200 to the treatment area and/or the spot diameter of laser radiation 204. In another embodiment, handpiece 200 may include a temperature sensing transducer on the distal end of space limiting accessory 216 for continuously monitoring temperature on the skin at the treatment area. In FIG. 2b a frontal view of handpiece 200 shows cooling system canal 220 used by cooling system 206 for delivering cooling medium, such as air. Cooling system canal 220 is preferably placed between handpiece outer case 210 and waveguide 202, such as a laser fiber optic. Cooling system canal 220 allows for uniform cooling medium delivery around laser radiation 204. In another embodiment, space limiting accessory 216 can be regulated in distance relative to the skin continuously, with the aid of a spring attached to handpiece outer case 210 from the proximal end of space limiting accessory 216, and continuous scale 218 on handpiece 200 shows the distance from the emitting end of handpiece 200 to the treatment area and/or the spot diameter of laser radiation 204.

In another embodiment, a device for transdermal treatment comprises a radiation source, preferably a laser radiation source with two different wavelength ranges. One laser wavelength preselected from a range of 980 to 1940 nm is preferred in order to provide adequate tissue penetration with sufficient energy to heat water inside target vessels and denature proteins, such as collagen. Another laser wavelength range preferred for the transdermal laser device comprises laser wavelengths that can be used in the generation of photomechanical waves, in order to induce an increase of skin permeability without affecting cell viability. Laser radiation in the range of 980 to 1940 nm is transmitted from the laser source to the handpiece with the aid of waveguide, such as an optical fiber whereas laser radiation of wavelength aimed to generate photomechanical waves is transmitted from the laser source to the skin with the aid of the same or another waveguide, such as an optical fiber. In order to increase skin permeability and enhance chemical composition delivery the patch or gel containing the chemical composition is covered with a target material. The target material completely absorbs the laser radiation of wavelength aimed to generate photomechanical waves so that the stratum corneum of the skin is exposed only to the photomechanical waves generated by the laser.

Figure 3A:
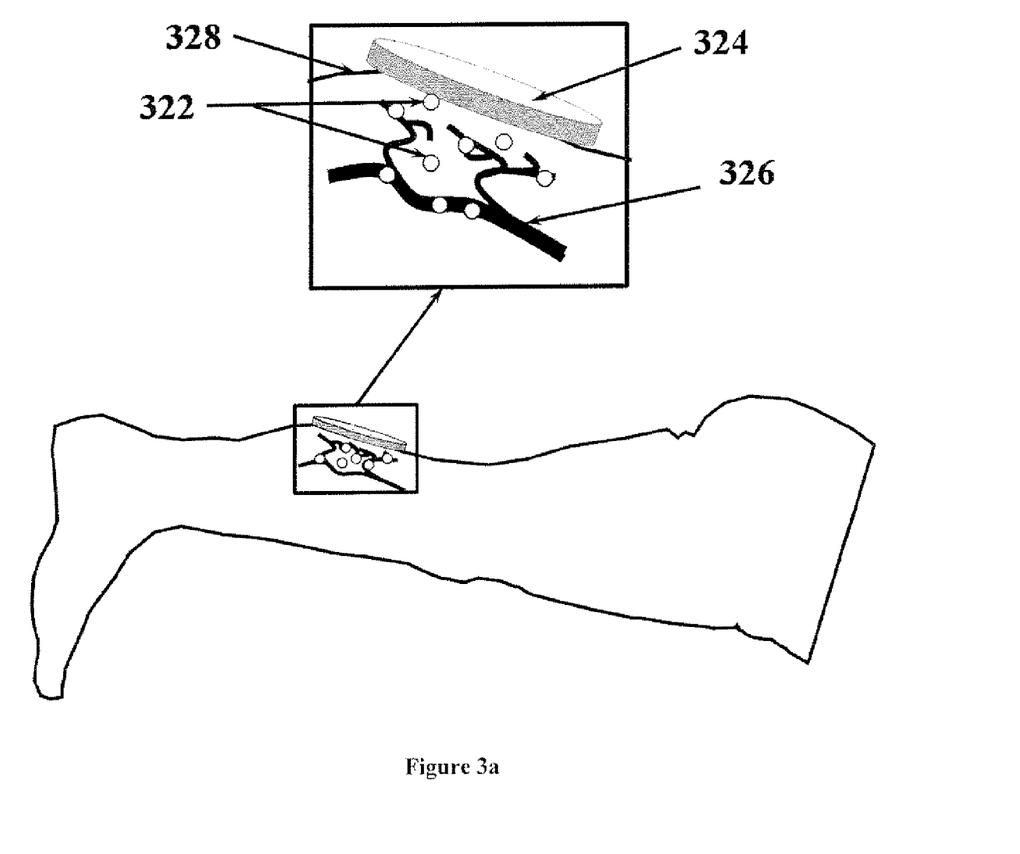
FIG. 3a illustrates an embodiment of the totally non-invasive transdermal method where a chemical composition is delivered transdermally to the treated zone.
Figure 3B:
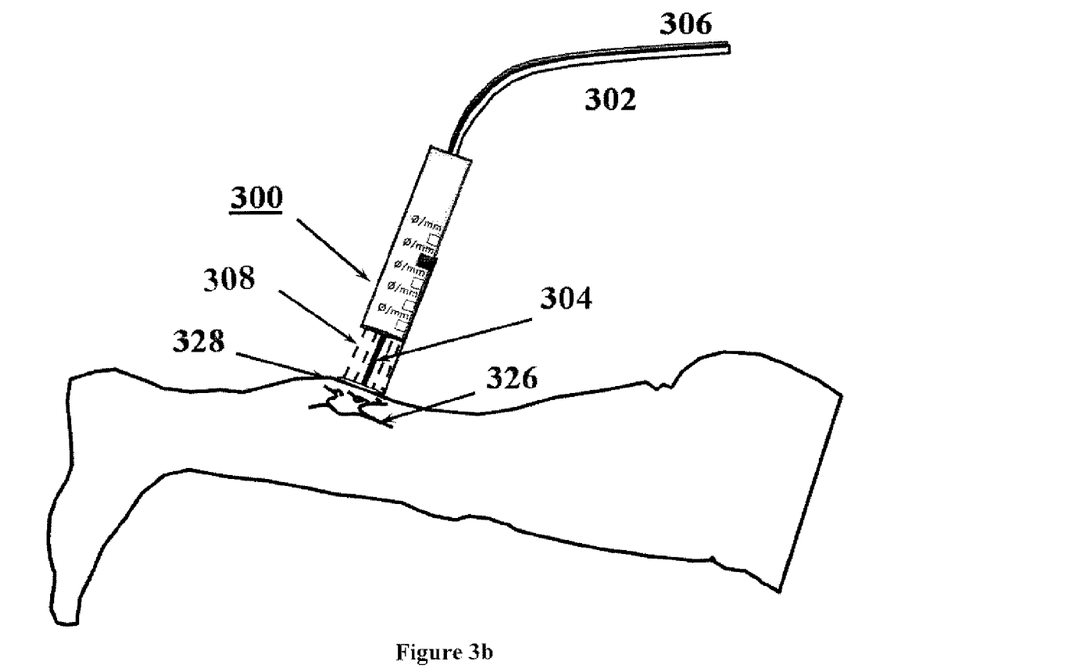
FIG. 3b illustrates an embodiment where laser energy is delivered transdermally to the treated zone, with the aid of a handpiece.

In a preferred embodiment shown in FIGS. 3a and b, the transdermal method for treating varicose veins comprises the transdermal delivery of chemical composition 322 with the aid of gel or patch 324 placed over varicose vein 326 to be treated. Then, the treated zone is cooled down either with cooling medium 308 produced by a cooling system 306 connected to handpiece 300 while lasing or with an aqueous cooling gel included in chemical composition 322. Immediately after or simultaneously with the absorption of chemical composition 322 through skin 328, laser radiation 304 of wavelength between about 980 and 1940 nm is delivered transdermally to the treated area with the aid of handpiece 300 connected to waveguide 302, causing the shrinkage or complete closure of treated varicose vein 326. Of particular use are lasers operating at 1470±50 nm. The shrinkage percentage or closure of varicose vein 326 treated is evaluated before and after treatment. Preferably, main component of the chemical composition delivered through the skin comprises hypertonic saline solution, a chromophore and/or any other substance that can absorb the emitted radiation and/or may damage the vessel endothelium. An important benefit of using hypertonic solution as a main component of the chemical composition is its limited contraindications due to the possibility of changing their content depending on the general condition of the patient. Moreover, unlike commonly used sclerosing agents, a hypertonic solution does not damage the skin nor produce pigmentation at the site of injection, does not cause an allergic reaction to the patient and has the advantage of being approved by the FDA. Radiation may be delivered by pulses with irradiance depending on the requirements of each specific clinical case.

Figure 3C:
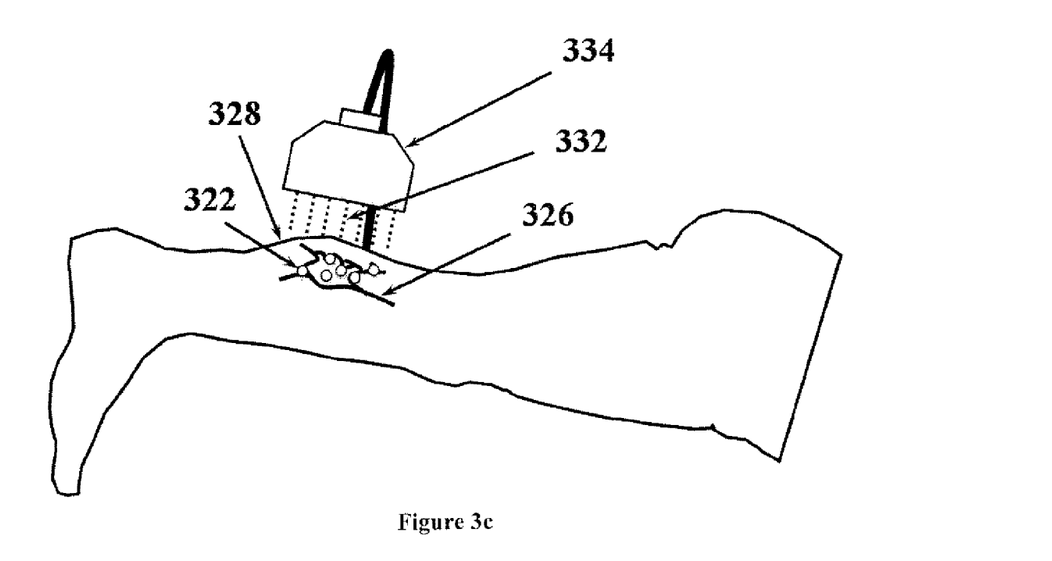
FIG. 3c shows another embodiment where radiation energy is delivered transdermally to the treated zone, with the aid of a LED lamp.

In another preferred embodiment shown in FIG. 3c, the transdermal method for treating varicose veins comprises the transdermal delivery of chemical composition 322 with the aid of gel or patch placed over varicose vein 326 to be treated. Then, the treated zone is cooled down with a cooling medium such as an aqueous cooling gel included in chemical composition 322. Immediately after or simultaneously with the absorption of chemical composition 322 through skin 328, radiation energy 332 of wavelength between about 980 and 1940 nm is delivered transdermally to the treated area with the aid of a LED lamp 334, causing the shrinkage or complete closure of treated varicose vein 326.

Figure 4A:
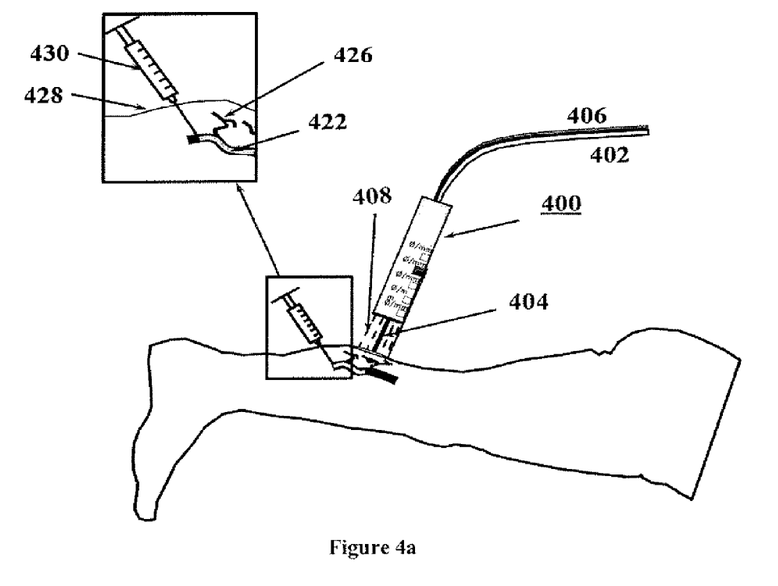
FIG. 4a shows another embodiment of a minimally-invasive transdermal method where a chemical fluid is injected with the aid of a syringe into the vein to be treated and laser energy is delivered transdermally with the aid of handpiece.

In another preferred embodiment shown in FIG. 4a, the method comprises the transdermal delivery of chemical fluid 422 directly to varicose vein 426 to be treated, with the aid of syringe 430. Then, the treated zone is cooled down either with an aqueous cooling gel or with cooling medium 408 produced by a cooling system 406 connected to handpiece 400 while lasing. Immediately after or simultaneously with the injection of chemical fluid 422, laser radiation 404 of wavelength between 980 and 1940 nm is guided through a waveguide 402 to handpiece 400 and delivered transdermally onto the skin 428 of the treated area, causing the shrinkage or complete closure of treated varicose vein 426. Again, the shrinkage percentage or closure of the varicose vein treated may be evaluated before and after the treatment and for following clinical evaluations. Preferably, the chemical fluid consists of a 20% hypertonic saline solution, a chromophore and/or any other substance that can absorb the emitted radiation and/or may damage the vessel endothelium. Radiation may be delivered by pulses with irradiance, depending on the requirements of each specific clinical case. As the total laser energy delivered to the treated zone is reduced compared to prior art techniques, the present invention provides methods and device that avoid damage to adjacent areas achieving better results in lesser time.

Figure 4B:
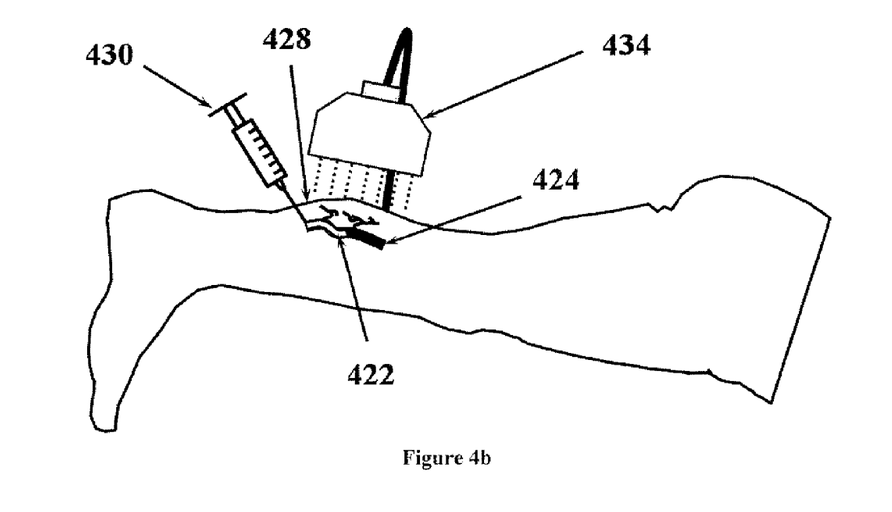
FIG. 4b shows another embodiment of a minimally-invasive transdermal method where a chemical fluid is injected with the aid of a syringe and radiation energy is delivered transdermally with the aid of a LED lamp.

In another preferred embodiment shown in FIG. 4b, the method comprises the transdermal delivery of chemical fluid 422 directly to varicose vein 424 to be treated, with the aid of syringe 430. Then, the treated zone is cooled down either with an aqueous cooling gel or with cooling medium. Immediately after or simultaneously with the injection of chemical fluid 422, radiation energy of wavelength between 980 and 1940 nm is delivered transdermally onto the skin 428 of the treated area with the aid of a LED lamp 434, causing the shrinkage or complete closure of treated varicose vein 424.

In another embodiment shown, a transdermal method for treating varicose veins and telangiectasias comprises the steps of: 1) exfoliating the skin of the area to be treated; 2) cooling the area to be treated either with an aqueous cooling gel or with cooling medium; 3) delivering radiation energy transdermally onto the skin of the treated area, causing the shrinkage or complete closure of treated varicose vein or telangiectasia. Radiation energy of wavelength about 980 and 1940 nm is preferably guided through a waveguide and delivered with the aid of handpiece or delivered with the aid of light emitting diodes lamps, incandescent, xenon arc and metal halide lamps. Once again, due to the low absorption of laser radiation by melanin about 980 and 1940, there is no ecchymosis, hematomas or hyper-pigmentation of the skin while performing transdermal treatment of spider veins and telangiectasias.

In a preferred embodiment, a chemical fluid for transdermal delivery is an aqueous solution, more preferably hypertonic or isotonic solutions based on distilled water. The aqueous hypertonic solution preferably containing on the basis of 100 milliliters of solution about 171.1 to 427.75 mmol sodium, about 171.1 to 427.75 mmol chloride and injectable water cps 100 ml, the solution having a pH between 4.5-7 and an osmotic pressure of about 3.42 to 8.55 Osm/l; more preferably containing on the basis of 100 milliliters of solution 342 mmol sodium, 342 mmol chloride and injectable water cps 100 ml, the solution having a pH between 4.5-7 and an osmotic pressure of 6.84 Osm/l. This corresponds to a range of hypertonic solutions whose lower limit is about 10% and upper limit is about 25%. The preferred concentration corresponds to about 20%.

In another preferred embodiment, a chemical composition for transdermal delivery comprises an active substance that can absorb the emitted radiation, i.e. a chromophore, and/or may damage the vessel endothelium i.e. hypertonic saline solution. Chemical composition formulation includes, but it is not limited to excipients and chemical enhancers such as hydrocarbons, sulphoxides, fatty acids, surfactants, esters and alcohols that can improve active substance flux across human skin. In order to improve transdermal delivery through human skin active substance may comprise, but it is not limited to an ion-pair compound, saturated or supersaturated solutions, eutectic systems and/or complexes with other substances; or may be encapsulated in vesicles such as liposomes, transfersomes or nanoparticles. Additional physical enhancement techniques may be used for improving transdermal delivery such as iontophoresis, electroporation, ultrasound, photomechanical waves, radiofrequency, magnetic fields, micro-needles, jet-propulsion or by any other means.

The present invention has several advantages. Mainly, it provides a transdermal ambulatory treatment of varicose veins with a completely non-invasive technique in the case of transdermal delivery of a chemical composition and transdermal light irradiation; and a minimally-invasive technique consisting of the injection of a chemical fluid and transdermal light irradiation. Moreover, the present invention provides a method with a single radiation source that allows the transdermal treatment of varicose blood vessels with a diameter that up to now could only be treated with surgery or endovascular laser treatments. Furthermore, owing to the lower laser energies used in this invention, the surrounding tissues of the treated areas remain practically undamaged. Thus, the present invention enhances prior art techniques for treating varicose veins offering a transdermal device and method that reduces discomfort to the patient and efficiently shrink or close treated varicose veins causing irreversible fibrosis to the blood vessel wall.

The present invention is further illustrated by the following examples, but is not limited thereby.

EXAMPLE 1

First, an aqueous cold gel is deposited onto the zone to be treated. Then, 1-2 cc of chemical solution is injected into the varicose vein having a diameter between 0.8-1 mm. The chemical composition is composed of an aqueous hypertonic solution containing on the basis of 100 milliliters of solution 342.2 mmol sodium, 342.2 mmol chloride and injectable water cps 100 ml, the solution having a pH between 4.5-7 and an osmotic pressure of 6.84 Osm/1. Immediately after injection, with the aid of a handpiece, laser radiation of 1470 nm is delivered to the treated zone by pulses with a 1 mm spot size and a pulse width of 0.45 s ON and 0.045 s OFF. Total energy delivered was 20 J during 16 s with a power level of 1 W. A vein reduction from 0.8 mm to 0.2 mm was observed immediately after treatment with the aid of echographic images.

EXAMPLE 2

First, the zone to be treated is cooled down. Then, 1-2 cc of a chemical solution is injected into the varicose vein having a diameter between 1.3-1.4 mm. The chemical composition is composed of an aqueous hypertonic solution containing on the basis of 100 milliliters of solution 342.2 mmol sodium, 342.2 mmol chloride and injectable water cps 100 ml, the solution having a pH between 4.5-7 and an osmotic pressure of 6.84 Osm/l. Immediately after injection, with the aid of a handpiece, laser radiation of 1470 nm is delivered to the treated zone by pulses with a 1 mm spot size and a pulse width of 0.45 s ON and 0.045 s OFF. Total energy delivered was 44 J during 41 s with a power of 1 W. Complete vein closure was observed after treatment with the aid of echographic images.

EXAMPLE 3

A chemical solution is injected into the varicose vein having a diameter between 3-4 mm, located approximately 10 mm underneath the skin. The chemical composition is composed of an aqueous hypertonic solution containing on the basis of 100 milliliters of solution 342.2 mmol sodium, 342.2 mmol chloride and injectable water cps 100 ml, the solution having a pH between 4.5-7 and an osmotic pressure of 6.84 Osm/1. Immediately after injection, laser radiation of 1470 nm is delivered to the treated zone by pulses, with a 1 mm spot size and a pulse width of 0.45 s ON and 0.045 s OFF. A handpiece was used to delivered laser radiation and for cooling down the treated zone while irradiating. The total energy delivered was 210 J during 178 s with a power of 2 W. Complete vein closure was observed and telangiectasia nutritious vein was shrunk.

EXAMPLE 4

After exfoliating the area to be treated, a cryogenic gel is applied onto the skin. Then, laser radiation of 1470 nm is delivered to the treated zone by pulses, with a 1 mm spot size and a pulse width of 10 ms ON and 0.6 s OFF. The power used to eliminate the telangectasia was 14 W. Complete telangectasia elimination vein closure was observed.

EXAMPLE 5

A chemical solution is injected into the varicose vein having a diameter between 3-4 mm. The chemical composition is composed of an aqueous hypertonic solution containing on the basis of 100 milliliters of solution 342.2 mmol sodium, 342.2 mmol chloride and injectable water cps 100 ml, the solution having a pH between 4.5-7 and an osmotic pressure of 6.84 Osm/1. Immediately after injection, laser radiation of 1470 nm is delivered to the treated zone by pulses, with a 1 mm spot size and a pulse width of 0.45 s ON and 0.045 s OFF. A handpiece was used to delivered laser radiation and for cooling down the treated zone while irradiating. The total energy delivered was 210 J during 178 s with a power of 2 W. Complete vein closure was observed and telangiectasia nutritious vein was shrunk.

Having described preferred embodiments of the invention with reference to the accompanying drawings, it is to be understood that the invention is not limited to the precise embodiments, and that various changes and modifications may be effected therein by one skilled in the art without departing from the scope or spirit of the invention as defined in the appended claims.

What is claimed is:

1. A method for treating vascular disorders transdermally, comprising the steps of:
   transdermally delivering a chemical composition to a vein in a treatment zone, said chemical composition comprising a hypertonic solution and a substance designed to absorb radiation; and
   irradiating the treatment zone transdermally with a radiation source capable of providing radiation at a power level of at least one (1) Watt and at least one wavelength, preselected from a range of 980 nm to 1940 nm.

2. The method according to claim 1, further comprising steps of:
   cooling said treatment zone, and evaluating said treatment zone using an echographic image.

3. The method according to claim 2, wherein said cooling of treatment zone is by application of aqueous cold gel transdermally on skin.

4. The method according to claim 2, wherein said cooling of treatment zone is done using a cooling system delivered by said handpiece.

5. The method according to claim 1, wherein said irradiating step employs a handpiece.

6. The method according to claim 5, wherein said handpiece is optically coupled to said radiation source using an optical fiber.

7. The method according to claim 1, wherein said chemical composition is administered through skin using one of a gel, patch and syringe.

8. The method according to claim 1, wherein said chemical composition further comprises a lidocaine solution.

9. The method according to claim 1, wherein said preselected wavelength is 1470±50 nm.

10. The method according to claim 1, wherein said vascular disorders comprise veins with a diameter of not more than 10-12 mm.

* * * * *